United States Patent [19]
Phillips

[11] Patent Number: 5,207,693
[45] Date of Patent: May 4, 1993

[54] ENDOSCOPIC SUTURE DISPENSING TOOL

[76] Inventor: Edward H. Phillips, 712 N. Roxbury, Beverly Hills, Calif. 90210

[21] Appl. No.: 780,486

[22] Filed: Oct. 23, 1991

[51] Int. Cl.⁵ .............................................. A61B 17/00
[52] U.S. Cl. ...................................... 606/146; 606/148
[58] Field of Search ................................ 606/146, 148

[56] References Cited

U.S. PATENT DOCUMENTS

| | | | |
|---|---|---|---|
| 373,372 | 11/1887 | La Forest King | 606/146 |
| 3,013,559 | 12/1961 | Thomas | 606/146 |
| 4,011,873 | 3/1977 | Hoffmeister | 606/146 |
| 4,935,027 | 6/1990 | Yoon | 606/146 |

Primary Examiner—Stephen C. Pellegrino
Assistant Examiner—Jeffrey A. Schmidt
Attorney, Agent, or Firm—Frederick Gotha

[57] ABSTRACT

An endoscopic suture tool is provided to minimize extra-corporeal exposure of the suture to bacteria and to minimize the possibility of suture entanglement with external trocars and other instruments. The suture tool has a holder with a protrubing hub for accepting a standard suture reel and an orifice through which the suture feeds into and through the lumen of an extension member releasably carried by the holder. Adjacent the distal end of the extension member, a slot is located in the extension member for captively and releasably holding the free end of the suture.

9 Claims, 3 Drawing Sheets

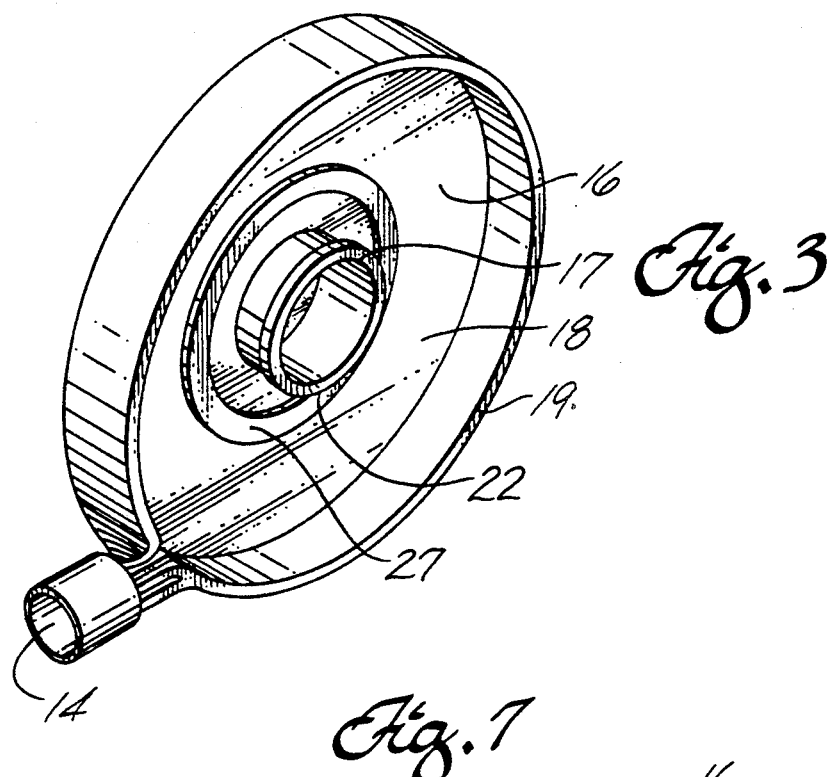
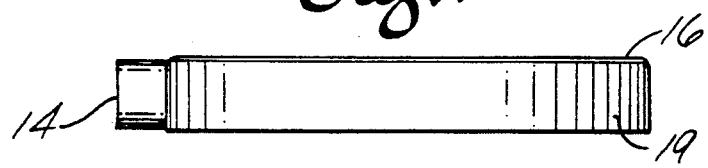
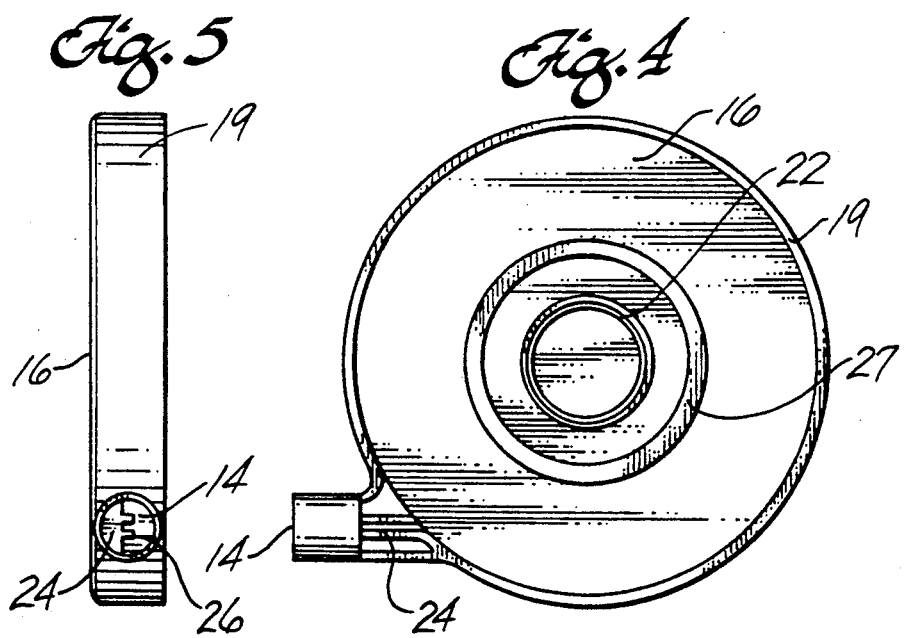
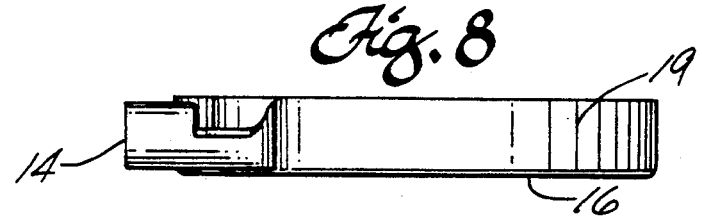

ENDOSCOPIC SUTURE DISPENSING TOOL

FIELD OF THE INVENTION

This invention relates to a suturing tool for use in endoscopic surgery.

BACKGROUND OF THE INVENTION

In order to suture endoscopically the suture material must be introduced through a trocar to the operative area where the free end of the suture is then manipulated laparoscopically around a body structure and then returned by passage through the trocar extra-corporeally of the patient. After emergence from the trocar the free end of the suture is then used to create a knot about the strand of suture material extending into the operative area from the suture reel, and the knot is then pushed through the trocar back into the operative space and toward the body structure to enable the surgeon to form a ligature. The length of the suture material to create a ligature laparoscopically in the prior art could require at least 4 feet of exposed suture material of which 2 to 3 feet of the suture would be draped over the abdomen of the patient. Thus, the laparoscopic suturing procedure of the prior art exposes the patient to an increased risk of bacterial infection and the consequent possibility of tissue damage while also creating increased operative risks because of the possibility of entanglement of the suture with external trocars and instruments.

SUMMARY OF THE INVENTION

There is, therefore, provided according to the present invention, an endoscopic suturing tool which permits the surgeon to introduce suture material laparoscopically into the operative area and after placing the free end of the suture material around a body structure in the operative area to withdraw the free end through a trocar and outside the body so as to minimize extra corporeal exposure of the suture to bacteria and to minimize the possibility of entanglement.

The present invention is directed to an endoscopic suture tool which is composed of a holder having a circumferential wall that forms a peripheral boundary for the holding region of the tool. A hub projects from the base of the holder into the holding region of the tool and the hub is adapted for accepting a standard reel of suture material so as to permit the reel to rotate relative to the hub. An orifice is located in the peripheral wall of the holder and is radially spaced from the axis of the hub. An extension member having an axis of extension and an axially extending lumen or channel is carried by the holder such that the lumen or channel communicates with the orifice at the proximate end of the extension member to permit the passage of suture material from the reel and into the lumen. The extension member has a peripheral slot in its outer surface adjacent its distal end for captively and releasably holding the suture at its free end after the free end has been placed around the body structure in the operative area. Thus, the suture is introduced into the operative area by passing through a channel or lumen contained within the extension member where the extension member gains access to the operative area by passing through a trocar. After introduction to the operative space the free end of the suture is then placed around a body structure i.e. blood vessel and then inserted laparoscopically into the peripheral slot contained adjacent the distal end of the extension member such that the free end is captively and releasably held; the extension member is then withdrawn through the trocar while the reel of suture is caused to rotate and continues until the free end of the suture emerges from the trocar. The free end is then used to form a knot extra-corporeally with the captive strand portion of the suture material extending from the reel and the knot is then returned to the operative region through the trocar.

BRIEF DESCRIPTION OF THE DRAWINGS

These and other features and advantages will become appreciated as the same become better understood with reference to the following specification, claims and drawings wherein:

FIG. 3 is a perspective view of the holder member of this invention.

FIG. 4 is a front view of the holder member which is shown in perspective in FIG. 3.

FIG. 5 is a left side view of FIG. 4.

FIG. 6 is a right side view of FIG. 4.

FIG. 7 is a top view of FIG. 4 and;

FIG. 8 is a bottom view of FIG. 4.

DETAILED DESCRIPTION

Figure 1:
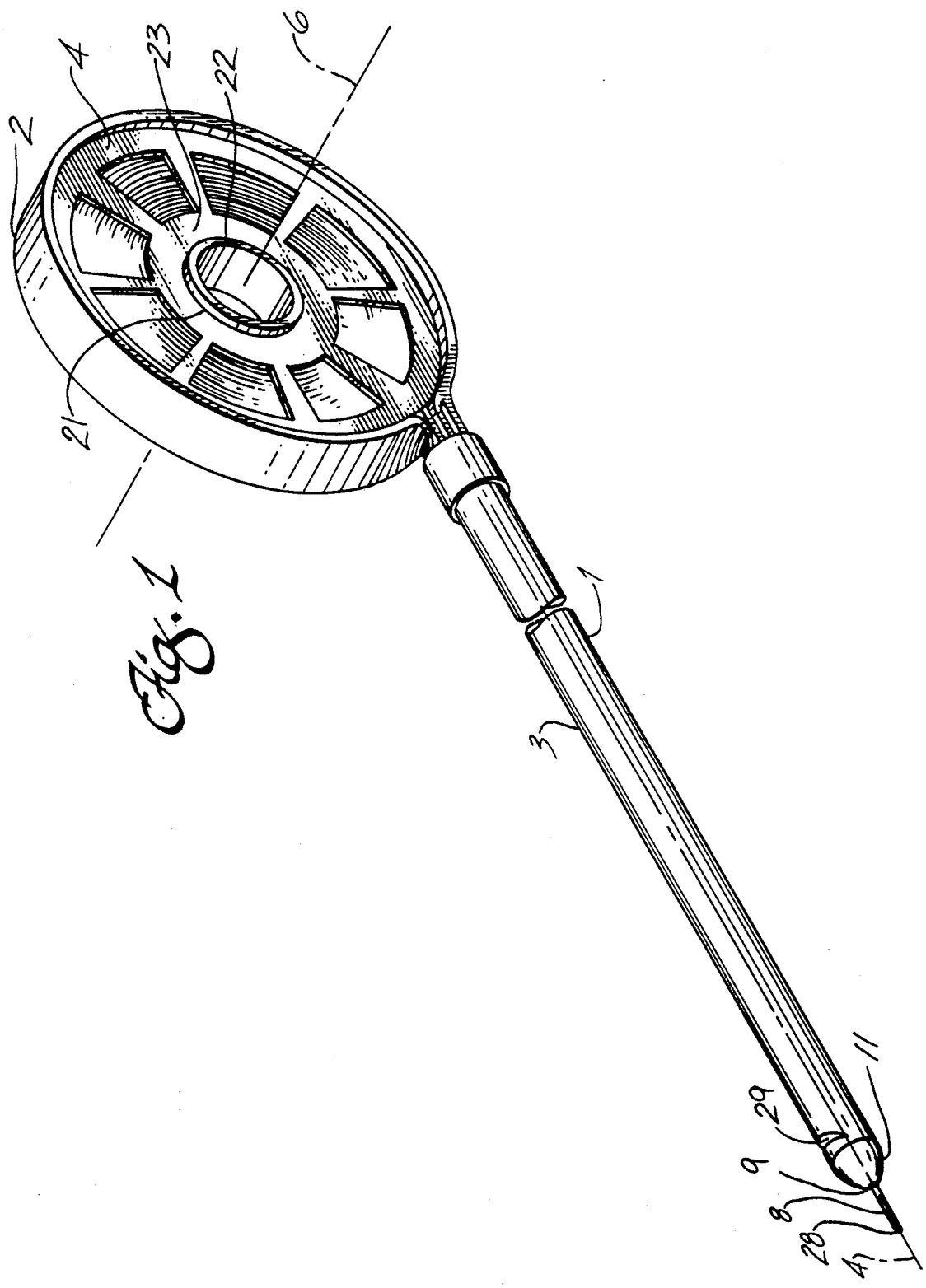
FIG. 1 is a perspective view of the endoscopic suture tool of this invention.

Referring to FIG. 1, a perspective view is shown of an endoscopic suture tool 1 which is composed of a holder 2 and an extension member 3 having an axis of elongation 4. Holder member 2 has a central axis 6 about which a standard reel of suture material 7 is permitted to rotate when the suture feeds through opening 9 located in the distal tip 11 of extension member 3.

Figure 2:
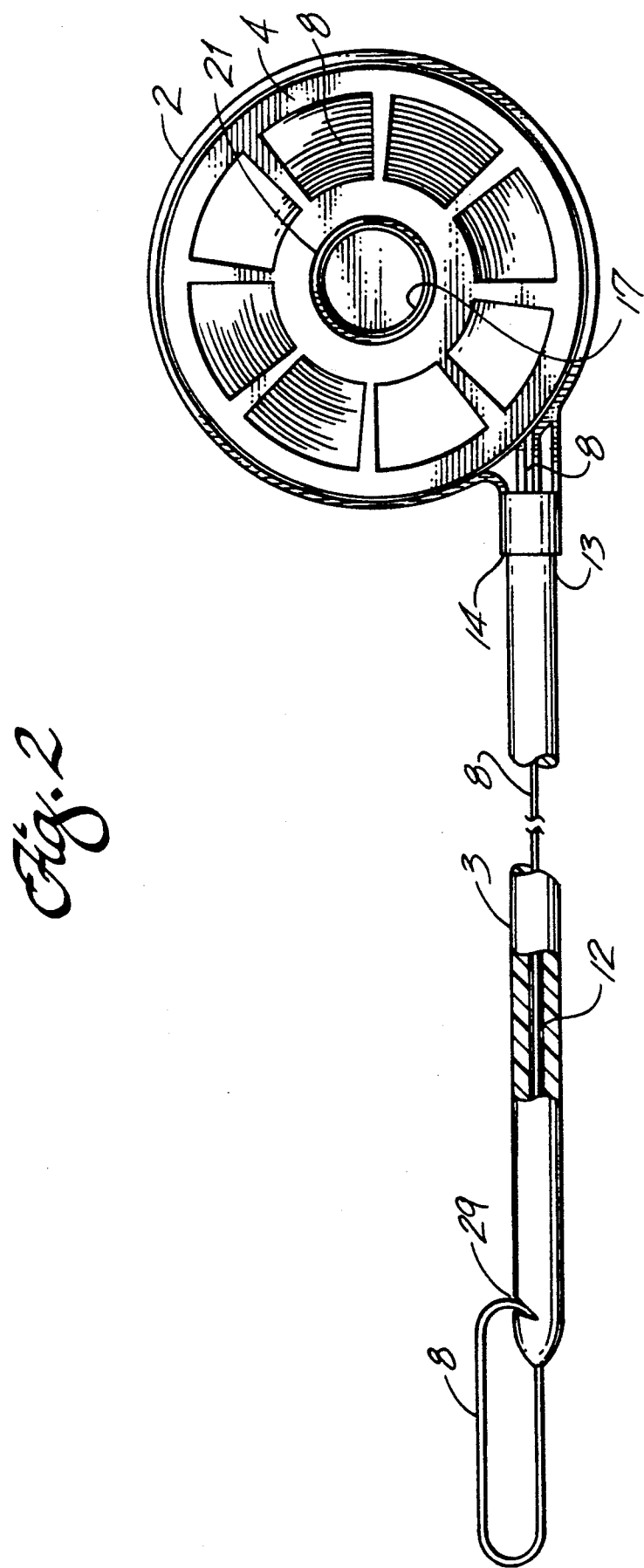
FIG. 2 is a left side view of FIG. 1.

As more clearly illustrated in FIG. 2, extension member 3 contains an axially extending channel or lumen 12 through which the suture 8 feeds in order to gain access to the operative area. Extension member 3 is preferably made of a plastic material. The proximate end 13 of extension member 3 captively inserts into orifice 14 of holder member 2 so as to permit Communication between the lumen or channel 12 and orifice 14. Although the extension member is frictionally held in the disclosed mode of the invention, the proximate end 13 could also be threaded for threaded engagement with orifice 14.

As can be seen in FIG. 3, holder 2 is comprised of a base member 16 which has an axially extending hub 17 that protrubes into the holder region 18 of the holder. A circumferential wall 19 extending axially from base member 16 forms the peripheral boundary of the holding region 18. The reel 7 containing the suture 8 is readily available from all suture manufacturers in a standard size and has a central aperature 21 for insertion onto hub 17 so as to permit relative rotation between reel 7 and the hub. Although not shown in the drawings, hub 17 may be removably mounted to base member 16 by threaded fit for example, to permit circumferential shoulder 22 to bear upon mounting disc 23 of reel 7 to releasably hold the reel within the holding region 18.

Referring now to FIG. 4 a guide member 24 is positioned within orifice 14 of holder 2 to guide the suture 8 through orifice 14 and into the lumen or channel 12 of extension member 3. As can be seen in FIG. 5, guide member 24 has a U-shaped channel 26 through which the suture feeds through orifice 14 and into the lumen or channel of extension member 3.

In order to reduce the frictional resistance of the reel as it revolves about hub 17, a bearing surface 27 is provided in base member 16. The bearing surface is radially and circumferentially spaced from hub 17 and the plane of the surface is axially spaced from base member 16.

In operation, the standard reel 7 containing suture material 8 is mounted to hub 17. The free end of the suture 28 is threaded through U-channel 26 and orifice 14 and through lumen or channel 12 of extension member 3 and the free end is then inserted into slot 28. The extension member is then inserted through a trocar (not shown) and the distal end 11 of the extension member is thereby laparoscopically introduced into the operative area within the body. The surgeon thereafter using an appropriate laparoscopic tool grasps the free end 28 of the suture which is then placed around a body structure in the operative area. The free end 28 is then inserted into slot 29 where the suture is releasably and captively held. The endoscopic suture tool is then withdrawn by the surgeon from the trocar and as the extension member passes through the trocar the reel 7 is rotated relative to the holder to feed suture material through the lumen or channel 18 as the extension member is withdrawn. When extension member 3 is withdrawn from the trocar, the surgeon then grasps the free end 28 of the suture and extra-corporeally forms a knot about the captive end suture strand extending from the reel and the knot is then forced through the trocar by the surgeon and into the operative region where the knot is then manipulated by the surgeon to form a ligature.

Thus, an endoscopic suture tool is provided which permits the formation of an extra corporeal knot while minimizing the exposure of the suture to bacterial elements and minimizing the possibility of entanglement with external trocars and other instruments.

While I have shown and described an embodiment of the present endoscopic suture tool, it is to be understood that it is subject to many modifications without departing from the scope and spirit of the claims as recited herein.

What is claimed is:

1. A suture tool for transporting the free-end of a reel of suture through a sheath to the operative region of a patient and for withdrawing the free-end through said sheath in the process of endoscopically forming a loop of suture or bight around a body structure in said region around which a ligature is to be formed, compromising:
   a) a holder having a central axis and a cavity therein defining a holding region for holding a reel of suture having a central aperture where said holder contains an orifice radially spaced from said central axis and communicating with said holding region for guiding the passage of a suture having a free end, from said holding region,
   b) a hub having a hub-axis coincident with said central axis carried by said holder and extending axially into aid holding region for accepting said reel of suture where said hub is positioned within said holding region to accept said central aperture of said reel of suture such that said reel of suture may be releasably and rotationally mounted to said hub to permit rotation of said reel about said hub-axis relative to said holder; and
   c) an extension member carried by said holder having a longitudinal axis and an axially extending lumen therethrough where said longitudinal axis extends in a direction lateral to said hub-axis and is radially spaced therefrom, said extension member having a distal end and a proximate end where said distal end has a distal opening therein communicating with said lumen and where said proximate end has a proximate opening therein communicating with said lumen and said orifice to permit the passage of said suture through said extension member; and
   d) retaining means, disposed in the external surface of said extension member and located adjacent to and proximately spaced from said distal opening, for releasably holding said free-end of said suture at a fixed distance from said distal end during passage of said suture through said distal opening while said suture tool is withdrawn through a sheath, whereby upon withdrawal of said extension member through said sheath, said reel of suture may be rotated relative to said holder to permit said free-end to be withdrawn through said sheath while being held by said retaining means at said fixed distance from said distal end during passage of said suture through said distal opening.

2. The endoscopic suture tool recited in claim 1 where said retaining means comprises a slot having an opening in said external surface of said extension member and of sufficient depth therein to captively hold said free-end of said suture.

3. The endoscopic suture tool recited in claim 1 wherein said extension member is releasably carried by said holder.

4. The endoscopic suture tool recited in claim 1 where said hub means is releasably carried by said holder.

5. A suture tool for transporting suture through a sheath to the operative region of a patient and thereafter endoscopically forming a loop of suture of bight around a body structure in said operative region around which a ligature is to be formed and thereafter withdrawing said suture such that said suture remains in looped engagement with said body structure comprising in combination:
   a) a reel of suture having a central aperture;
   b) a holder having a central axis and a cavity therein defining a holding region for holding said reel of suture wherein said holder contains an orifice radially spaced from said central axis and communicating with said holding region for guiding the passage of said suture from said holding region;
   c) a hub having a hub-axis coincident with said central axis carried by said holder and extending axially into said holding region for accepting said reel of suture where said hub is positioned within said holding region to accept said central aperture of said reel of suture such that said reel of suture may be releasably and rotationally mounted to said hub to permit a rotation of said reel of suture about said hub-axis relative to said holder;
   d) an extension member carried by said holder having a longitudinal axis and an axially extending lumen therethrough where said longitudinal axis extends in a direction lateral to said hub-axis and is radially spaced therefrom, said extension member having a distal end and a proximate end where said distal end has a distal opening therein communicating with said lumen and where said proximate end has a proximate opening therein communicating with said lumen and said orifice to permit the passage of said suture through said extension member; and e) retaining means disposed in the external surface of said extension member and located adjacent to and proximately spaced from said distal opening for releasably holding a free-end of said suture at a fixed distance from said distal end during passage of said suture through said distal opening while said suture tool is withdrawn through a sheath, whereby upon withdrawal of said extension member through said sheath, said reel of suture may be rotated relative to said holder to permit said free-end to be withdrawn through said sheath while being held by said retaining means at said fixed distance from said distal end during passage of said suture through said distal opening.

6. The combination recited in claim 5 where said retaining means comprises a slot having an opening in said external surface of said extension member and of sufficient depth therein to captively hold said free-end of said suture.

7. The combination recited in claim 5 wherein said extension member is releasably carried by said holder.

8. The combination recited in claim 5 wherein said hub means is releasably carried by said holder.

9. A method for endoscopically forming a loop of suture or bight around a body structure located within the internal operative region of a patient such that a ligature may be formed during endoscopic surgery, comprising the steps of:

a) attaching a free-end of a reel of suture extra-corporeally to an external surface of an extension member such that said free-end is releasably and captively held by said extension member at a fixed distance from the distal end of said extension member;

b) transporting said free-end while captively held by said extension member through a sheath where said sheath is positioned to extend through the abdomen of said patient and to communicate with said internal operative region;

c) grasping and releasing said free-end with an endoscopic grasping tool and endoscopically looping said free-end while in the grasp of said grasping tool around said body structure to form a bight;

d) re-attaching said free-end endoscopically to said external surface of said extension member such that said free-end is releasably and captively held at a fixed distance from the distal end of said extension member;

e) withdrawing said free-end while captively held at said fixed distance from said distal end of said extension member through said sheath and rotating said reel of suture during said withdrawal thereby permitting said free-end to be withdrawn extra-corporeally of said patient while captively held at said fixed distance and permitting said bight to remain in looped relationship with said body structure around which a ligature is to be formed.

* * * * *